US005723578A

United States Patent [19]
Coy et al.

[11] Patent Number: 5,723,578
[45] Date of Patent: Mar. 3, 1998

[54] PEPTIDE ANALOGS OF BOMBESIN

[75] Inventors: David H. Coy, New Orleans, La.; Jacques-Pierre Moreau, Upton; Sun Hyuk Kim, Needham, both of Mass.

[73] Assignees: The Administrators of Tulane Educational Fund, New Orleans, La.; Biomeasure Incorporated, Milford, Mass.

[21] Appl. No.: 488,099

[22] Filed: Jun. 7, 1995

Related U.S. Application Data

[63] Continuation-in-part of Ser. No. 337,127, Nov. 10, 1994, which is a continuation-in-part of Ser. No. 779,039, Oct. 18, 1991, abandoned, which is a continuation-in-part of Ser. No. 502,438, Mar. 30, 1990, Pat. No. 5,084,555, which is a continuation-in-part of Ser. No. 397,169, Aug. 21, 1989, abandoned, which is a continuation-in-part of Ser. No. 376,555, Jul. 7, 1989, abandoned, which is a continuation-in-part of Ser. No. 317,941, Mar. 2, 1989, abandoned, which is a continuation-in-part of Ser. No. 282,328, Dec. 9, 1988, Pat. No. 5,162,497, which is a continuation-in-part of Ser. No. 257,998, Oct. 14, 1988, abandoned, which is a continuation-in-part of Ser. No. 248,771, Sep. 23, 1988, abandoned, which is a continuation-in-part of Ser. No. 207,759, Jun. 16, 1988, abandoned, which is a continuation-in-part of Ser. No. 204,171, Jun. 8, 1988, abandoned, which is a continuation-in-part of Ser. No. 173,311, Mar. 25, 1988, abandoned, which is a continuation-in-part of Ser. No. 100,571, Sep. 24, 1987, abandoned.

[51] Int. Cl.$^6$ .................. A61K 38/00; C07K 5/00; C07K 7/00; C07K 17/00
[52] U.S. Cl. .................... 530/326; 530/327; 530/328
[58] Field of Search .................. 530/328, 326, 530/327

[56] References Cited

U.S. PATENT DOCUMENTS 5,244,883  9/1993  Cai et al. .................. 514/15

FOREIGN PATENT DOCUMENTS

| 0 434 979 A1 | 7/1991 | European Pat. Off. | C07K 7/02 |
| 0 468 497 A2 | 1/1992 | European Pat. Off. | C07K 7/06 |
| WO92/02545 | 2/1992 | WIPO | C07K 7/06 |
| WO92/20707 | 11/1992 | WIPO | C07K 7/02 |
| WO93/16105 | 8/1993 | WIPO | C07K 7/06 |
| WO94/21674 | 9/1994 | WIPO | C07K 7/08 |

OTHER PUBLICATIONS

Bado et al., "Possible Mediation by Luminal Somatostatin of Bombesin–Induced Satiety in the Cat", Am. J. Physiol. 263 (Regulatory Integrative Com. Physiol. 32): R84–R88, 1992.

Coy et al., "Probing Peptide Backbone Function in Bombesin", Journal of Biological Chemistry, 11:5056–5060, 1988.

Coy et al., "Progress in the Development of Competitive Bombesin Antagonists", Annals of the New York Academy of Sciences, 547:150–157, 1988.

Coy et al., "Systematic Development of Bombesin/Gastrin–Releasing Peptide Antagonists", Journal of the National Cancer Institute Monographs, 13:133–139, 1992.

Coy et al., "Short–Chain Pseudopeptide Bombesin Receptor Antagonists with Enhanced Binding . . . ", The Journal of Biological Chemistry, 264:14691–14697, 1989.

Cuber et al., "Blockade of Bombesin Receptors with . . . ", Peptides, 11:255–258, 1990.

Dickinson et al., "Partial Agonist Activity of the Bombesin–Receptor Antagonist . . . ", Biochemical and Biophysical Research Communications, 157:1154–1158, 1988.

Edwards et al., "Potent Pseudopeptide Bombesin–like Agonists and Antagonists", Int. J. Peptide Protein Res. 43:374–383, 1994.

Mahmoud et al., "Small Cell Lung Cancer Bombesin Receptors are Antagonized By Reduced Peptide Bond Analogues" Life Sciences, 44:367–373, 1989.

Mahmoud et al., "[Psi$^{13,14}$] Bombesin Analogues Inhibit Growth of Small Cell Lung Cancer *in Vitro* and *in Vivo*", Cancer Research, 51:1798–1802, 1991.

Rossowski et al., "Effects of a Novel Bombesin Antagonist Analogue on Bombesin–Stimulated Gastric Acid . . . ", Scand. J. Gastroenterol. 24:121–128, 1989.

Severi et al., "Pharmacological Characterization of . . . ", The Journal of Pharmacology and Experimental Therapeutics, 251:731–717, 1989.

Trepei et al., "A Novel Bombesin Receptor Antagonist Inhibits Autocrine Signals in a Small Cell Lung Carcinoma Cell Line", Biochem. & Biophys. Res. Comm. 156:1383–1389, 1988.

Woll et al., "[Leu$^{13}$Ψ(CH$_2$NH)Leu$^{14}$] Bombesin is a Specific Bombesin Receptor Antagonist in Swiss 3T3 Cells", Biochem. and Biophysical Res. Comm., 155:359–365, 1988.

*Primary Examiner*—Avis M. Davenport
*Attorney, Agent, or Firm*—Fish & Richardson P.C.

[57] ABSTRACT

Linear peptide analogs of bombesin with modified amino acid residues at various positions. A peptide of a group of bombesin analogs according to this invention contains either a —CH$_2$NH$_2$— pseudopeptide bond, a (3S,4S)-4-amino-3-hydroxy- 6-methylheptanoic acid residue, or a (3S,4S)-4-amino-3- hydroxy-5-phenylpentanoic acid residue.

21 Claims, No Drawings

PEPTIDE ANALOGS OF BOMBESIN

BACKGROUND OF THE INVENTION

This application is a continuation-in-part of U.S. patent application Ser. No. 08/337,127 filed Nov. 10, 1994, now pending, which in turn is a continuation-in-part of U.S. patent application Ser. No. 07/779,039 filed Oct. 18, 1991, now abandoned which in turn is a continuation-in-part of U.S. patent application Ser. No. 07/502,438 filed Mar. 30, 1990 issued as U.S. Pat. No. 5,084,555, which in turn is a continuation-in-part of U.S. patent application Ser. No. 07/397,169 filed Aug. 21, 1989, now abandoned, which in turn is a continuation-in-part of U.S. patent application Ser. No. 07/376,555 filed Jul. 7, 1989, now abandoned, which in turn is a continuation-in-part of U.S. patent application Ser. No. 07/317,941 filed Mar. 2, 1989, now abandoned, which in turn is a continuation-in-part of U.S. patent application Ser. No. 07/282,328 filed Dec. 9, 1988, issued as U.S. Pat. No. 5,162,497, which in turn is a continuation-in-part of U.S. patent application Ser. No. 07/257,998 filed Oct. 14, 1988, now abandoned, which in turn is a continuation-in-part of U.S. patent application Ser. No. 07/248,771 filed Sep. 23, 1988, now abandoned, which in turn is a continuation-in-part of U.S. patent application Ser. No. 07/207,759 filed Jun. 16, 1988, now abandoned, which in turn is a continuation-in-part of U.S. patent application Ser. No. 07/204,171 filed Jun. 8, 1988, now abandoned, which in turn is a continuation-in-part of U.S. patent application Ser. No. 07/173,311 filed Mar. 25, 1988, now abandoned, which in turn is a continuation-in-part of U.S. patent application Ser. No. 07/100,571 filed Sep. 24, 1987, now abandoned.

This invention relates to therapeutic peptides useful, e.g., in cancer therapy or inflammation.

The amphibian peptide bombesin (Anastasi et al., Experientia 27:166–167 (1971)) is closely related to the mammalian gastrin-releasing peptides (GRP), e.g., the porcine GRP (McDonald et al., Biochem. Biophys. Res. Commun. 90:227–233 (1979)). Bombesin has been found to be an autocrine or paracrine mitotic factor for a number of human cancer cell lines, including small-cell lung carcinoma (SCLC) (Haveman et al., eds. *Recent Results in Cancer Research—Peptide Hormones in Lung Cancer*, Springer-Verlag, New York:1986). A number of these cancers are known to secrete peptide hormones related to GRP or bombesin. Consequently, both agonists and antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice (Cuttitta et al., Cancer Survey 4:707–727 (1985)). In 3T3 murine fibroblasts which are responsive to the mitotic effect of bombesin, Zachary and Rozengurt observed that a substance P antagonist (Spantide) acted as a bombesin antagonist (Zachary et al., Proc. Natl. Acad. Sci. (USA), 82:7616–7620 (1985)). Heinz-Erian et al. replaced His at position 12 in bombesin with D-Phe and observed bombesin antagonist activity in dispersed acini from guinea pig pancreas (Heinz-Erian et al., Am. J. of Physiol. 252:G439–G442 (1987)). Rivier reported on work directed toward restricting the conformational freedom of the bioactive C-terminal decapeptide of bombesin by incorporating intramolecular disulfide bridges; however, Rivier mentioned that, so far, bombesin analogs with this modification fail to exhibit any antagonist activity (Rivier et al., "Competitive Antagonists of Peptide Hormones," in Abstracts of the International Symposium on Bombesin-Like Peptides in Health and Disease, Rome (October, 1987).

SUMMARY OF THE INVENTION

The present invention relate to peptide analogs of bombesin.

A class of peptides of this invention is of the generic formula:

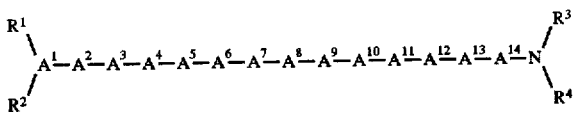

wherein $A^1$ is D- or L- isomer of pGlu, or deleted;

$A^2$ is Gln, Asn, Gly, Ala, Leu, Ile, Nle, Abu, Met, Val, Phe, p-X-Phe in which X is F, Cl Br, OH, or $CH_3$, Trp, β-Nal, or deleted;

$A^3$ is the D- or L- isomer selected from Arg and Lys, or deleted;

$A^4$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^5$ is Gly, the D- or L- isomer selected from Gln, Asn, Ala, Leu, Ile, Nle, Abu, Met, Val, Phe, D-Phe, p-X-Phe in which X is F, Cl, Br, OH, or $CH_3$, Trp and β-Nal, or deleted;

$A^6$ is Gly, the D- or L- isomer selected from Gln, Asn, Ala, N—Ac-D-Ala, Leu, Ile, Nle, Abu, Met, Val, Phe, p-X-Phe in which X is F, Cl, Br, OH, or $CH_3$, pentafluoro-Phe, Trp, p-Glu, and β-Nal, or deleted;

$A^7$ is Gly, or the D- or L- isomer selected from Gln, Asn, Ala, Leu, Ile, Nle, Abu, Met, Val, Phe, D-Phe, p-X-Phe in which X is F, Cl, Br, OH, or $CH_3$, Trp, Lys, His, Saa, and β-Nal;

$A^8$ is Trp or Met;

$A^9$ is Sta, AHPPA, Gly, or the D- or L- isomer selected from Gln, Asn, Gly, Ala, Leu, Ile, Nle, Abu, Met, Val, Phe, p-X-Phe in which X is F, Cl, Br, OH, or $CH_3$, Trp, and β-Nal;

$A^{10}$ is Sta, AHPPA, Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Sta, AHPPA, Gly, or the D- or L- isomer selected from Ala, Eaa, and Phe;

$A^{12}$ is Sta, AHPPA, or the D- or L- isomer selected from His, Phe, and p-X-Phe in which X is F, Cl, Br, OH, or $CH_3$;

$A^{13}$ is Sta, AHPPA, Gly, or the D- or L- isomer selected from Gln, Asn, Gly, Ala, Lew, Ile, Nle, Abu, Met, Val, Phe, p-X-Phe in which X is F, Cl, Br, OH, or $CH_3$, Trp, Tic, Tip, Oic, Tcc, and β-Nal;

$A^{14}$ is Gln, Asn, Gly, Ala, Leu, Ile, Nle, Abu, Met, Val, Phe, p-X-Phe in which X is F, Cl, Br, OH, or $CH_3$, Trp, Tic, Tip, Oic, Tcc, or β-Nal;

each of $R^1$ and $R^2$, independently, is H, $C_{1-12}$ alkyl, $C_{7-10}$ phenylalkyl, $CO.E_1$ in which $E_1$ is $C_{1-20}$ alkyl, $C_{2-20}$ alkenyl, $C_{2-20}$ alkynyl, phenyl, naphthyl, or $C_{7-10}$ phenylalkyl, or $CO.OE_2$ in which $E_2$ is $C_{1-10}$ alkyl or $C_{7-10}$ phenylalkyl; and each of $R^3$ and $R^4$, independently, is H, $C_{1-12}$ alkyl, or $C_{7-10}$ phenylalkyl;

provided that when one of $R^1$ or $R^2$ is $CO.E_1$ or $CO.OE_2$, the other must be H; further provided that when $A^1$ is pGlu, one of $R^1$ and $R^2$ must be H and the other must be the portion of pGlu that forms the imine ring, and when the N-terminal amino acid is Saa, one of $R^1$ and $R^2$ must be the $N^\alpha$-substitutent of said Saa; provided that either the carbon atom participating in the amide bond between one and only one pair of neighboring amino acids selected from the group consisting of $A^7$ and $A^8$, $A^8$ and $A^9$, $A^9$ and $A^{10}$, $A^{11}$ and $A^{12}$, $A^{12}$ and $A^{13}$, and $A^{13}$ and $A^{14}$ is a methylene carbon, or one and only one of $A^9$, $A^{10}$, $A^{11}$, $A^{12}$, and $A^{13}$ is Sta or AHPPA; and further provided that the next higher numbered amino acid residue adjacent to Sta or AHPPA must be deleted (for example, if $A^9$ is Sta or AHPPA, then $A^{10}$ must be deleted); or a pharmaceutically acceptable salt thereof.

Another class of peptides of this invention is also covered by the above generic formula, except that $A^7$ is limited to Saa and $A^{13}$ includes two additional variables D-Pro and L-Pro. The above formula further covers a third class of peptides of this invention, except that $A^{11}$ is limited to Sta, AHPPA and Eaa and $A^{13}$ further includes two more variables D-Pro and L-Pro. Thus, a peptide of one of the three classes described above either contains one and only one pseudopeptide bond, i.e., —$CH_2NH$—, or contains one and only one Sta or AHPPA residue.

A fourth class of peptides also has the same generic formula, except that $A^1$ through $A^4$ are deleted and $A^5$ through $A^{14}$ contain respectively the following assignments:

$A^5$ is Gln, Asn, Gly, Ala, Leu, Ile, Nle, Abu, Met, Val, Phe, D-Phe, p-X-Phe in which X is F, Cl, Br, OH, or $CH_3$, Trp, β-Nal, or deleted;

$A^6$ is Gln, Asn, Gly, Ala, D-Ala, N—Ac-D-Ala, Leu, Ile, Nle, Abu, Met, Val, Phe, p-X-Phe in which X is F, Cl, Br, OH, or $CH_3$, Trp, p-Glu, Trp, β-Nal, or deleted;

$A^7$ is Gln, Asn, Gly, Ala, Leu, Ile, Nle, Abu, Met, Val, Phe, D-Phe, p-X-Phe in which X is F, Cl, Br, OH, or $CH_3$, Trp, Lys, His, Saa, or β-Nal;

$A^8$ is Trp or Met;

$A^9$ is the D- or L-isomer selected from Gln, Asn, Gly, Ala, Leu, Ile, Nle, Abu, Met, Val, Phe, p-X-Phe in which X is F, Cl, Br, OH, or $CH_3$, Trp, and β-Nal;

$A^{10}$ is Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Gly, or the D- or L- isomer selected from Ala, Phe, and Eaa;

$A^{12}$ is the D- or L- isomer selected from His, Phe, and p-X-Phe in which X is F, Cl, Br, OH, or $CH_3$;

$A^{13}$ is Gln, Asn, Gly, Ala, Leu, Ile, Nle, Abu, Met, Val, Phe, p-X-Phe in which X is F, Cl, Br, OH, or $CH_3$, Trp, Tic, Tip, Oic, Tcc, or β-Nal; and $A^{14}$ is Gln, Asn, Gly, Ala, Leu, Ile, Nle, Abu, Met, Val, Phe, p-X-Phe in which X is F, Cl, Br, OH, or $CH_3$, Trp, Tic, Tip, Oic, Tcc, or β-Nal.

The fourth class of peptides further differs from the other classes in that a peptide of this class either contains a —$CH_2NH$—pseudopeptide bond between $A^{13}$ and $A^{14}$ or does not contain any pseudopeptide bond.

Particularly preferred peptides of the invention include the following (the —$CH_2NH$—pseudopeptide bond is symbolized herein by "Ψ"):

pGlu-Gln-Arg-Leu-Gly-Asn-Gln-Trp-Ala-Val-Gly-His-Ψ-Leu-Leu-NH₂ (BIM-26025);

pGlu-Gln-Arg-Leu-Gly-Asn-Gln-Trp-Ala-Ψ-Val-Gly-His-Leu-Leu-NH₂ (BIM-26026);

pGlu-Gln-Arg-Leu-Gly-Asn-Gln-Trp-Ala-Val-Gly-His-Leu-Ψ-Leu-NH₂ (BIM-26028);

pGlu-Gln-Arg-Leu-Gly-Asn-Gln-Trp-Ala-Val-Gly-Ψ-His-Leu-Leu-NH₂ (BIM-26030);

Arg-Leu-Gly-Asn-Gln-Trp-Ala-Ψ-Val-Gly-Phe-Leu-Met-NH₂ (BIM-26036);

pGlu-Gln-Arg-Leu-Gly-Asn-Gln-Trp-Ala-Val-Gly-Ψ-D-Phe-Leu-Leu-NH₂ (BIM-26046);

D-pGlu-Trp-Ala-Val-D-Ala-His-Leu-Ψ-Met-NH₂ (BIM-26061);

pGlu-Gln-Arg-Leu-Gly-Asn-Gln-Trp-Ala-Val-Gly-His-Phe-Ψ-Leu-NH₂ (BIM-26062);

pGlu-Gln-Arg-Leu-Gly-Asn-Trp-Ala-Val-Gly-His-Leu-Ψ-Met (BIM-26063);

pGlu-Gln-Arg-Leu-Gly-Asn-Gln-Trp-Ala-Val-Gly-D-Phe-Leu-Ψ-Leu-NH₂ (BIM-26065);

pGlu-Gln-Arg-Leu-Gly-Asn-Trp-Ala-Val-Gly-His-Leu-Ψ-Leu-NH₂ (BIM-26067);

pGlu-Gln-Arg-Leu-Gly-Asn-Gln-Trp-Ala-Val-Gly-His-Leu-Ψ-Phe-NH₂ (BIM-26068);

pGlu-Gln-Arg-Tyr-Gly-Asn-Gln-Trp-Ala-Val-Gly-His-Leu-Ψ-Met-NH₂ (BIM-26071);

pGlu-Gln-Arg-Leu-Gly-Asn-Trp-Ala-Val-Gly-His-Leu-Ψ-Leu-NH₂ (BIM-26074);

pGlu-Gln-Arg-Leu-Gly-Asn-Gln-Trp-Ala-Val-D-Phe-His-Leu-Ψ-Leu-NH₂ (BIM-26075);

pGlu-Gln-Arg-Leu-Gly-Asn-Gln-Trp-Ala-Val-D-Phe-His-Leu-Ψ-Leu-NH₂ (BIM-26076);

pGlu-Gln-Arg-Leu-D-Ala-Asn-Gln-Trp-Ala-Val-Gly-His-Leu-Ψ-Leu-NH₂ (BIM-26077);

pGlu-Gln-Arg-Leu-Gly-Asn-Gln-Trp-Ala-Val-D-Ala-His-Leu-Ψ-Leu-NH₂ (BIM-26078);

pGlu-Gln-Arg-Leu-Gly-Asn-Gln-Trp-Ala-Val-Gly-D-Phe-Leu-Ψ-Leu-NH₂ (BIM-26086);

pGlu-Gln-Arg-Leu-Gly-Asn-Gln-Trp-Ala-Val-Gly-His-Leu-Ψ-Phe-NH₂ (BIM-26087);

Gly-Asn-His-Trp-Ala-Val-Gly-His-Leu-Ψ-Met-NH₂ (BIM-26092);

D-Ala-Asn-His-Trp-Ala-Val-Gly-His-Leu-Ψ-Met-NH₂ (BIM-26093);

pGlu-Gln-Arg-Leu-D-Ala-Asn-Gln-Trp-Ala-Val-D-Ala-His-Leu-Ψ-Leu-NH₂ (BIM-26094);

pGlu-Gln-Trp-Ala-Val-D-Ala-His-Leu-Ψ-Leu-NH₂ (BIM-26095);

Ac-Lys-Trp-Ala-Val-Gly-His-Leu-Ψ-Met-NH₂ (BIM-26097);

Lys-Trp-Ala-Val-Gly-His-Leu-Ψ-Met-NH₂ (BIM-26098);

pGlu-Gln-Arg-Leu-Gly-Asn-Gln-Trp-Ala-Val-Gly-His-Leu-Ψ-Met-NH₂ (BIM-26099);

pGlu-Gln-Trp-Ala-Val-Gly-His-Phe-Ψ-Leu-NH₂ (BIM-26100);

pGlu-Gln-Trp-Ala-Val-Gly-His-Leu-Ψ-Leu-NH₂ (BIM-26101);

Gly-Asn-Leu-Trp-Ala-Thr-Gly-His-Phe-Ψ-Met-NH₂ (BIM-26102);

His-Trp-Ala-Val-Gly-His-Leu-Ψ-Met-NH₂ (BIM-26104);

D-Ala-Asn-His-Trp-Ala-Val-D-Ala-His-Leu-Ψ-Met-NH₂ (BIM-26105);

D-Ala-His-Trp-Ala-Val-D-Ala-His-Leu-Ψ-Met-NH₂ (BIM-26106);

D-Phe-Asn-His-Trp-Ala-Val-Gly-His-Leu-Ψ-Met-NH₂ (BIM-26107);

Ac-D-Ala-Asn-His-Trp-Ala-Val-Gly-His-Leu-Ψ-Met-NH₂ (BIM-26108);

pGlu-Gln-Trp-D-Ala-Val-Gly-His-Phe-Ψ-Leu-NH₂ (BIM-26109);

D-Ala-His-Trp-Ala-Val-D-Ala-His-Phe-Ψ-Met-NH₂ (BIM-26110);

D-Nal-His-Trp-Ala-Val-D-Ala-His-Phe-Ψ-Phe-NH₂ (BIM-26111);

Asn-D-Phe-Trp-Ala-Val-Gly-His-Leu-Ψ-Leu-NH₂ (BIM-26112);

D-Phe-Gln-Trp-Ala-Val-Gly-His-Leu-Ψ-Leu-NH₂ (BIM-26113);

D-Nal-Gln-Trp-Ala-Val-Gly-His-Leu-Ψ-Leu-NH₂ (BIM-26114);

Phe-D-Phe-Gln-Trp-Ala-Val-Gly-His-Leu-Ψ-Leu-NH₂ (BIM-26115);

D-Phe-His-Trp-Ala-Val-D-Ala-His-Leu-Ψ-Leu-NH₂ (BIM-26116);

D-Nal-His-Trp-Ala-Val-D-Ala-His-Leu-Ψ-Leu-NH₂ (BIM-26117);

pGlu-Gln-Trp-D-Ala-Val-D-Ala-His-Phe-Ψ-Leu-NH₂ (BIM-26119);

Gly-Asn-Leu-Trp-Ala-Thr-Gly-His-Phe-Ψ-Met-NH₂ (BIM-26121);

pGlu-Gln-Arg-Leu-Gly-D-Phe-Gln-Trp-Ala-Val-Gly-His-Leu-Ψ-Leu-NH₂ (BIM-26133);

D-Nal-Gln-Trp-Ala-Val-Gly-His-Leu-Ψ-Phe-NH₂ (BIM-26136);

D-Nal-Gln-Trp-Ala-Val-Gly-His-Leu-Ψ-Nal-NH₂ (BIM-26137);

Asn-Gln-Trp-Ala-Val-Gly-His-Leu-Ψ-Leu-NH₂ (BIM-26138);

Gly-Asn-Gln-Trp-Ala-Val-Gly-His-Leu-Ψ-Leu-NH₂ (BIM-26139);

D-Phe-Gln-Trp-Ala-Val-Gly-His-Leu-Ψ-Phe-NH₂ (BIM-26157);

Phe-Gln-Trp-Ala-Val-Gly-His-Leu-Ψ-Phe-NH₂ (BIM-26158);

D-Cpa-Gln-Trp-Ala-Val-Gly-His-Leu-Ψ-Phe-NH₂ (BIM-26159);

Me-D-Phe-Gln-Trp-Ala-Val-Gly-His-Leu-Ψ-Phe-NH₂ (BIM-26161);

D-Phe-Gln-Trp-Ala-Val-Gly-His-Phe-Ψ-Leu-NH₂ (BIM-26166);

D-Phe-Gln-Trp-Ala-Val-Gly-His-Leu-Ψ-D-Cpa-NH₂ (BIM-26189);

D-Phe-Gln-Trp-Ala-Val-Gly-His-Leu-Ψ-D-Phe-NH₂ (BIM-26190);

D-Tyr-Gln-Trp-Ala-Val-Gly-His-Leu-Ψ-Phe-NH₂ (BIM-26256);

D-Pentafluoro-Phe-Gln-Trp-Ala-Val-D-Ala-His-D-Tic-Ψ-Tic-NH₂ (BIM-26323);

D-Pentafluoro-Phe-Gln-Trp-Ala-Val-D-Ala-His-D-Tic-Ψ-Phe-NH₂ (BIM-26327);

Phenylpropionyl-His-Trp-Ala-Val-D-Ala-His-Leu-Ψ-Leu-NH₂ (BIM-26346);

Phenylpropionyl-Trp-Trp-Ala-Val-D-Ala-His-Leu-Ψ-Leu-NH₂ (BIM-26347);

Phenylpropionyl-Pro-Trp-Ala-Val-D-Ala-His-Pro-Ψ-Phe-NH₂ (BIM-26358);

Phenylpropionyl-D-Pro-Trp-Ala-Val-D-Ala-His-Pro-Ψ-Phe-NH₂ (BIM-26359);

Phenylpropionyl-His-Trp-Ala-Val-beta-Ala-His-D-Pro-Ψ-Phe-NH₂;

pGlu-Gln-Arg-Leu-Gly-Asn-Gln-Trp-Ala-Val-Ψ-Gly-His-Leu-Leu-NH₂ (BIM-26027);

pGlu-Gln-Arg-Leu-Gly-Asn-Gln-Trp-Ala-Val-Gly-His-Sta-NH₂ (BIM-26096);

pGlu-Gln-Trp-Ala-Val-Gly-His-Sta-NH₂ (BIM-26120);

Gln-Trp-Ala-Val-Gly-His-Sta-NH₂ (BIM-26149);

D-Phe-Gln-Trp-Ala-Val-Gly-His-Ahppa-NH₂ (BIM-26163);

D-Phe-Gln-Trp-Ala-Val-Gly-His-Sta-NH₂ (BIM-26164);

D-Nal-Gln-Trp-Ala-Val-Gly-His-Sta-NH₂ (BIM-26150);

D-Cpa-Gln-Trp-Ala-Val-Gly-His-Sta-NH₂ (BIM-26173);

D-Cpa-Gln-Trp-Ala-Val-Sar-His-Sta-NH₂ (BIM-26186);

D-Arg-Pro-Lys-Pro-D-Phe-Gln-D-Trp-Gly-D-Trp-Sta-NH₂ (BIM-26207);

pGlu-Gln-Trp-Ala-Val-D-Ala-His-Sta-NH₂ (BIM-26208);

D-Phe-Gln-Trp-Ala-Phe-D-Ala-His-Sta-NH₂ (BIM-26209);

D-Phe-Gln-Trp-Ala-Val-D-Ala-His-Sta-NH₂ (BIM-26211);

Ac-His-Trp-Ala-Val-D-Ala-His-Sta-NH₂ (BIM-26249); and

Ac-Arg-Gln-Trp-Ala-Val-Gly-His-Sta-NH₂ (BIM-26255);

Note that, with the exception of an N-terminal amino acid residue, for all amino acid sequence formulas described herein, each amino acid residue, e.g., $A^3$ or Lys, represents the structure of —NH—C(R)H—CO—, in which R is the side chain. For an N-terminal amino acid residue, the symbol may represent NH₂—C(R)H—CO—(e.g., BIM-26036, supra), —NH—C(R)H—CO—(e.g., BIM-26255, supra), or =N—C(R)H—CO—(e.g., the generic formula). Lines between amino acid residues represent peptide bonds which join two amino acids. Also, where the amino acid residue is optically active, it is the L-form configuration that is intended unless D-form is expressly designated.

The uncommon abbreviations pGlu, Cpa, Nle, β-Nal, Sar, homo-Pro, Abu, Tcc, Tic, Tip, Oic, Sta, and AHPPA stand for, respectively, pyroglutamate, p-chloroPhenylalanine, norleucine, 3-(β-naphthyl)alanine, sarcosine, 2-carboxylic-piperidine, α-aminobutyric acid, 1,2,3,4-tetrahydro-2-carboline-3-carboxylic acid, 1,2,3,4-tetrahydro-2-carboline-3-yl-carboxylic acid, 4,5,6,7-tetrahydro-1H-imidazo[c]pyridine-6-carboxylic acid, (3aS,7aS)- octahydroindol-2-yl-carboxylic acid, (3S,4S)-4-amino-3-hydroxy-6-methylheptanoic acid, and (3S,4S)-4-amino-3-hydroxy-5-Phenylpentanoic acid. Saa and Eaa, on the other hand, stand for a secondary amino acid and an extended amino acid, respectively. A secondary amino acid is an α-amino acid the non-side chain amino group of which is a secondary amine, e.g., Sar, N-Me-Ala, Pro, homoPro, Tic, Tcc, Tip, or Oic (but not pGlu). An extended amino acid is an amino acid which has more than one carbon atom, e.g., a straight chain of 2–5 carbons, linked between its non-side chain amino group and non-side chain carboxyl group, e.g., aminopentanoic acid, aminohexanoic acid, β-Ala, or γ-aminobutyric acid.

The peptides of the invention are suitable for the treatment of all forms of cancer where bombesin-related substances act as autocrine or paracrine mitotic factors, especially pancreas, prostate, breast, colon, and small-cell lung carcinoma. The peptides can also be used for the inhibition of gastric acid secretion, the symptomatic relief and/or treatment of exocrine pancreatic adenocarcinoma, and the restoration of appetite to cachexic patients.

The peptides can be administered to a human patient, via one of the traditional modes (e.g., orally, parenterally, transdermally, or transmucosally), in a sustained release formulation using a biodegradable biocompatible polymer, or by on-site delivery (e.g., in the case of anti-cancer bombesin to the lungs) using micelles, gels and liposomes. A reasonable dosage for a human patient ranges from 0.5 mg/kg/day to 5 mg/kg/day, and is to be determined by the attending physician based on various factors. For some forms of cancer, e.g., small-cell lung carcinoma, the preferred dosage for curative treatment is 250 mg/patient/day.

The peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acids, as well as polymeric acids such as tannic acid or carboxymethyl cellulose, and salts with inorganic acids such as the hydrohalic acids, e.g., hydrochloric acid, sulfuric acid, or phosphoric acid.

In addition, any of these analogs tagged with a radioactive label can be used for imaging tumors that express the bombesin receptor, e.g., small cell lung tumors. Additionally, these peptides can be used to test G.I. and cardiovascular disorders.

In the above generic formula, when $R_1$, $R_2$, $R_3$ or $R_4$ is an aromatic, lipophilic group, the in vivo activity can be long lasting, and delivery of the compounds of the invention to the target tissue (e.g., the lungs) can be facilitated.

DETAILED DESCRIPTION OF THE INVENTION

In general, the invention features a linear (i.e., non-cyclic) peptide which is an analog of a naturally occurring, biologically active peptide having an active site and a binding site responsible for the binding of the peptide to a receptor on a target cell, cleavage of a peptide bond in the active site of the naturally occurring peptide being unnecessary for in vivo biological activity, the analog having a non-peptide bond instead of a peptide bond between an amino acid of the active site and an adjacent amino acid, the analog being capable of binding to the receptor, so that the analog is capable of acting as a competitive inhibitor of the naturally occurring peptide by binding to the receptor and, by virtue of the non-peptide bond, failing to exhibit the in vivo activity of the naturally occurring peptide. A detailed discussion of the chemistry of non-peptide bonds can be found in Coy et al. (1988) Tetrahedron 44,3:835–841, hereby incorporated by reference.

Preferably, the naturally occurring peptide is characterized in that one or more amino acids in the amino terminal half of the peptide are hydrogen bonded to one or more amino acids in the carboxyl terminal half of the peptide, and the non-peptide bond of the linear peptide decreases that hydrogen bonding, thereby destroying biological activity. The linear peptides of the invention are analogs of peptides whose biological activity apparently depends at least in part on their ability to form tertiary "hairpin" configurations in which amino acids in the amino terminal ("left") half of the molecule are hydrogen bonded to amino acids in the carboxyl terminal ("right") half of the molecule, and that the pseudopeptide bond or Sta or AHPPA residue introduced according to the invention interferes with this hydrogen bonding, hindering the formation of the hairpin configuration on which activity depends.

Generally, useful classes of peptides which can be prepared by the introduction of a pseudopeptide bond are those in which at least one amino acid involved in the active site is located in the carboxyl terminal half of the molecule; the non-peptide bond is introduced between this amino acid and one adjacent to it.

Without further elaboration, it is believed that one skilled in the art can, based on the description herein, utilize the present invention to its fullest extent. Indeed, unless defined otherwise, all technical and scientific terms used herein have the same meaning as commonly understood by one of ordinary skill in the art to which this invention belongs. Methods and materials similar or equivalent to those described herein can be used in the practice or testing of the present invention. All publications, patent applications, patents, and other references mentioned herein are incorporated by reference. In addition, the materials, methods, and examples are illustrative only and not intended to be limiting.

Synthesis of Bombesin Analogs

The synthesis of peptides are within the scope of a skilled person in the art, and in any event, is readily available in the literature. For example, see, Stewart et al., Solid Phase Peptide Synthesis, Pierce Chemical, 2nd Ed. 1984. The peptide bond reduction method which yields a —$CH_2NH$— pseudopeptide bond is described in U.S. Pat. Nos. 4,803,261 and 4,897,445; and 5,059,653. All of the above publications are hereby incorporated by reference.

As an example, the synthesis of the bombesin analog pGlu-Gln-Arg-Leu-Gly-Asn-Gln-Trp-Ala-Val-Gly-His-Leu-Ψ-Leu-$NH_2$ (BIM-26028) follows. Other peptide analogs of bombesin can be prepared by making appropriate modifications of the following synthetic method.

The first step is the preparation of the intermediate pGlu-Gln-Arg(tosyl)-Leu-Gly-Asn-Gln-Trp-Ala-Val-Gly-His( benzyloxycarbonyl)-Leu-Ψ-Leu-benzhydrylamine resin, as follows.

Benzhydrylamine-polystyrene resin (Vega Biochemicals, Inc.) (0.97 g, 0.5 mmole) in the chloride ion form is placed in the reaction vessel of a Beckman 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin is stirred with α-t-butoxycarbonyl (Boc)-leucine and diisopropylcarbodiimide (1.5 mmole each) in methylene chloride for 1 hour, and the resulting amino acid resin is then cycled through steps (a) to (f) in the above wash program. Boc-leucine aldehyde (1.25 mmoles), prepared by the method of Fehrentz and Castro, Synthesis, p. 676 (1983), is dissolved in 5 ml of dry dimethylformamide (DMF) and added to the resin TFA salt suspension followed by the addition of 100 mg (2 mmoles) of sodium cyanoborohydride (Sasaki and Coy, Peptides 8:119–121 (1987); Coy et al., id.). After stirring for 1 hour, the resin mixture is found to be negative to ninhydrin reaction (1 min.), indicating complete derivatization of the free amino group.

The following amino acids (1.5 mmole) are then coupled successively in the presence diisopropylcarbodiimide (1.5 mmole), and the resulting amino acid resin is cycled through washing/deblocking steps (a) to (f) in the same procedure as above: Boc-His(benzyloxycarbonyl), Boc-Gly, Boc-Val, Boc-Ala, Boc-Trp, Boc-Gln (coupled in the presence of equivalent of hydroxybenzotriazole), Boc-Asn (coupled in the presence of 1 equivalent of hydroxybenzotriazole), Boc-Gly (coupled as a 6M excess of the p-nitroPhenyl ester), Boc-Leu, Boc-Arg(tosyl), Boc-Gln (coupled as a 6M excess of the p-nitroPhenylester), and pGlu. The completed resin is then washed with methanol and air dried.

The resin described above (1.6 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen, and free peptide is precipitated and washed with ether. The crude peptide is dissolved in a minimum volume of 2M acetic acid and eluted on a column (2.5×100 mm) of Sephadex G-25 (Pharmacia Fine Chemicals, Inc.). Fractions containing a major component by uv absorption and thin layer chromatography (TLC) are then pooled, evaporated to a small volume and applied to a column (2.5×50 cm) of octadecylsilane-silica (Whatman LRP-1, 15–20 mm mesh size).

The peptide is eluted with a linear gradient of 0–30% acetonitrile in 0.1% trifluoroacetic acid in water. Fractions are examined by TLC and analytical high performance liquid chromatography (HPLC) and pooled to give maximum purity. Repeated lyophilization of the solution from water gives 60 mg of the product as a white, fluffy powder.

The product is found to be homogeneous by HPLC and TLC. Amino acid analysis of an acid hydrolysate confirms the composition of the peptide. The presence of the Leu-$\Psi$-Leu bond is demonstrated by fast atom bombardment mass spectrometry.

pGlu-Gln-Arg-Leu-Gly-Asn-Gln-Trp-Ala-$\Psi$-Val-Gly-His-Leu-Met- $NH_2$ and pGlu-Gln-Arg-Leu-Gly-Asn-Gln-Trp-Ala-Val-Gly-His-Leu-$\Psi$-Met-$NH_2$ or other peptides are prepared in similar yields in an analogous fashion by appropriately modifying the above procedure.

A statine or AHPPA residue can be substituted in place of any two amino acids of the peptide, where the peptide contains no pseudopeptide bonds. For example, Sta$^{13}$-des Met$^{14}$ bombesin was prepared in an analogous fashion by first coupling statine to the resin and then proceeding with the addition of Boc-His(benzylocarbonyl). Statine or Boc-statine can be synthesized according to the method of Rich et al., 1978, J. Organic Chem. 43; 3624; and Rich et al., 1980, J. Med. Chem. 23: 27, and AHPPA can be synthesized according to the method of Hui et al., 1987, J. Med. Chem. 30: 1287.

As another example, the synthesis of Sta$^{13}$-Des Met$^{14}$ bombesin analog is set forth below:

Solid-phase synthesis of the peptide pGlu-Gln-Arg-Leu-Gly-Asn-Gln-Trp-Ala-Val-Gly-His-Sta-$NH_2$ (BIM-26096) was accomplished through the use of the following procedures in which alpha-t-butoxycarbonyl statine (prepared by the procedure of Rich et al., J. Org. Chem. 1978, 43, 3624) is first coupled to methylbenz-hydrylamine-polystyrene resin. After acetylation, the intermediate p-Glu-Gln-Arg (tosyl)-Leu-Gly-Asn-Gln-Trp-Ala-Val-Gly-His (benzyloxycarbonyl)-Sta-methylbenzhydrylamine resin is prepared. The synthetic procedure used for this preparation follows in detail:

1. Incorporation of alpha-t-butoxycarbonyl statine on methylbenzhydrylamine resin.

Methylbenzhydrylamine-polystyrene resin (Vega Biochemicals, Inc.) (1.0 g, 0.73 mmol) in the chloride ion form is placed in the reaction vessel of a Vega 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin is mixed for 18 hours with the preformed active ester made from alpha-t-butoxycarbonyl statine (1.46 mmol), diisopropyl carbodiimide (2 mmol), and hydroxybenzotriazole hydrate (1.46 mmol in dimethylformamide at 0° C. for one hour. The resulting amino acid resin is washed on the synthesizer with dimethylformamide and then methylene chloride. The resin mixture at this point was found by the Kaiser ninhydrin test (5 minutes) to have an 84% level of statine incorporation on the resin.

Acetylation was performed by mixing the amino-acid resin for 15 minutes with N-acetyl imidazole (5 mmol) in methylene chloride. Derivatization to the 94–99% level of the free amino groups of the resin was indicated by the Kaiser ninhydrin test (5 minutes). The Boc-statine-resin is then washed with methylene chloride.

2. Couplings of the Remaining Amino Acids.

The peptide synthesizer is programmed to perform the following reaction cycle: (a) methylene chloride; (b) 33% triflouroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (2.19 mmol) are then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin is washed on the synthesizer with dimethylformamide and then methylene chloride, and then cycled through the washing and deblocking steps (a) to (f) in the procedure described above.

Boc-His (benzyloxycarbonyl) (coupled in the presence of 2 equivalents hydroxybenzotriazole); Boc-Gly; Boc-Val; Boc-Ala; Boc-Trp; Boc-Gln and Boc Asn (coupled as the preformed hydroxybenzotriazole active esters made by reaction at 0° C. for one hour with 1 equivalent hydroxybenzotriazole hydrate); Boc-Gly; Boc-Leu; Boc-Arg(tosyl), Boc-Gln, and pGlu (also coupled as the preformed active esters of hydroxybenzotriazole made by reaction at 0° C. for one hour with 1 equivalent hydroxybenzotriazole hydrate). The completed peptide-resin is then washed with methanol and air dried.

The peptide-resin described above (1.60 g, 0.73 mmol) is mixed with anisole (2.5 mL), dithioerythreitol (50 mg), and anhydrous hydrogen fluoride (30 mL) at 0° C. for one hour. Excess hydrogen fluoride is evaporated rapidly under a stream of dry nitrogen, and the free peptide is precipitated and washed with ether. The crude peptide is dissolved in 100 mL of 1M acetic acid and the solution is then evaporated under reduced pressure. The crude peptide is dissolved in a minimum volume of methanol/water 1/1 and triturated with 10 volumes of ethyl acetate.

The triturated peptide is applied to a column (9.4 mm I.D.×50 cm) of octadecylsilane-silica (Whatman Partisil 10 ODS-2M 9). The peptide is eluted with a linear gradient of 20–80% of 20/80 0.1% trifluoroacetic acid/acetonitrile in 0.1% trifluoroacetic acid in water. Fractions are examined by TLC and analytical high performance liquid chromatography (HPLC) and pooled to give maximum purity. Lyophilization of the solution from water gives 77 mg of the product as a white fluffy powder.

Other compounds can be prepared as above and tested for effectiveness as agonists or antagonists in the following test programs.

GRP Receptor Binding Assay

Membranes for the GRP receptor binding assay were obtained by homogenizing cultured AR42J cells (Polytron, setting 6, 15 sec) in ice-cold 50 mM Tris-HCl (Buffer A) and centrifuging twice at 39,000×g (10 min), with an intermediate resuspension in fresh buffer. The final pellets were resuspended in the 50 mM Tris-HCl, containing 0.1 mg/ml bacitracin, and 0.1% BSA (Buffer B), and held on ice for the receptor binding assay. For assay, aliquots (0.4 ml) were incubated with 0.05 ml [$^{125}$I-Tyr$^4$] bombesin (~2200 Ci/mmol, New England Nuclear) and Buffer B, with and without 0.05 ml of unlabeled competing peptides. After a 30 min incubation (4° C.), the bound [$^{125}$I-Tyr$^4$] bombesin was separated from the free by rapid filtration through GF/B filters which had been previously soaked in 0.3% polyethyleneimine. The filters were then washed three times with 5 ml aliquots of ice-cold Buffer A. Specific binding was defined as the total [$^{125}$I-Tyr$^4$] bombesin bound minus that bound in the presence of 1 µM unlabeled bombesin. The IC$_{50}$ value was calculated as the concentration of the competing peptides required to inhibit 50 percent of the specific binding.

NMB Receptor Binding Assay

Membranes for the NMB receptor binding assay were obtained by homogenizing rat olfactory bulb tissue (Polytron, setting 6, 15 sec) in ice-cold 50 mM Tris-HCl (Buffer A) and centrifuging twice at 39,000×g (10 min), with an intermediate resuspension in fresh buffer. The final pellets were resuspended in the 50 mM Tris-HCl, containing 0.1 mg/ml bacitracin, and 0.1% BSA (Buffer B), and held on ice for the receptor binding assay. For assay, aliquots (0.4 ml) were incubated with 0.05 ml [$^{125}$I]NMB (~2200 Ci/mmol, New England Nuclear) and Buffer B, with and without 0.05 ml of unlabeled competing peptides. After a 30 min incubation (4° C.), the bound [$^{125}$I]NMB was separated from the free by rapid filtration through GF/B filters which had been previously soaked in 0.3% polyethyleneimine. The filters were then washed three times with 5 ml aliquots of ice-cold Buffer A. Specific binding, IC$_{50}$, was defined as the total [$^{125}$I]NMB bound minus that bound in the presence of 1 µM unlabeled NMB. The IC$_{50}$ value was calculated as the concentration of the competing peptides required to inhibit 50 percent of the specific binding.

Thymidine Incorporation Assay

Cultures of Swiss 3T3 cells were maintained in Dulbecco's modified Eagle's medium (DMEM) supplemented with 10% fetal bovine serum in a humidified atmosPhere of 7% CO2/90% air at 37° C. In preparation for assay, approximately 20,000 cells were subcultured in 24-well culture plates for and grown three to four days. For the determination of [$^3$H] thymidine incorporation into DNA, the cells were washed once with 1.0 ml aliquots of serum-free DMEM and incubated in this media for 24 hr. Fresh serum-free DMEM, containing [$^3$H]thymidine (1 µCi/ml, 1 µM) and peptides, was added, and the cells were incubated for an additional 24 hr at 37° C. At the end of the incubation, the cells were washed once with ice-cold saline, 5% trichloroacetic acid, and once with 95% ethanol. The acid-precipitable radioactive residue was dissolved in 0.1N NaOH and transferred to a liquid scintillation vial for counting. For antagonists, the IC$_{50}$ value was the concentration of test peptide which inhibited 50 percent of bombesin stimulated thymidine uptake. For agonists, the EC$_{50}$ is the concentration of test peptide which stimulated 50 percent of the maximum amount of thymidine uptake.

A number of analogs of bombesin were synthesized and tested in one or more of the above-described assays. The results of the GRP and NMB binding assays are given in Table I, which shows the results of in vitro inhibition of [$^{125}$I]GRP binding to AR42J cells and [$^{125}$I]NMB binding to rat olfactory bulb tissue. Table I also gives results from tests on the naturally-occurring peptides bombesin, neuromedin B, and GRP.

TABLE I

Binding Assays

| PEPTIDE | GRP(IC$_{50}$) nM | NMB(IC$_{50}$) nM |
|---|---|---|
| BOMBESIN | 1.88 | 17.15 |
| GRP | 1.55 | 252.25 |
| NMB | 15.85 | 1.71 |
| BIM-26025 | >1000 | N/A |
| BIM-26026 | >1000 | N/A |
| BIM-26027 | 0.48 | N/A |
| BIM-26028 | 38.67 | 3599 |
| BIM-26030 | 654 | >10,000 |
| BIM-26062 | 3.73 | 1267 |
| BIM-26068 | 2.90 | N/A |
| BIM-26071 | 34.00 | N/A |
| BIM-26100 | 5.21 | 8734 |
| BIM-26113 | 11.7 | 11503 |
| BIM-26114 | 29.7 | 6622 |
| BIM-26116 | 48.20 | >10,000 |
| BIM-26120 | 19.80 | >10,000 |
| BIM-26121 | 34.4 | 12483 |
| BIM-26136 | 5.41 | 462.7 |
| BIM-26156 | 19.2 | 2265 |
| BIM-26157 | 1.07 | 3405 |
| BIM-26158 | 3.39 | 2812 |
| BIM-26159 | 1.47 | 1682 |
| BIM-26161 | 2.52 | 4154 |
| BIM-26166 | 11.50 | 2042 |
| BIM-26173 | 4.25 | 24459 |
| BIM-26189 | 1.51 | 4426 |
| BIM-26327 | 21.95 | N/A |
| BIM-26346 | 33.31 | N/A |
| BIM-26347 | 54.76 | N/A |
| BIM-26358 | 3.65 | N/A |

In Table I, it can be seen that these peptides have a high affinity for the GRP receptor. The preferred placement of the non-peptide bond in bombesin analogs is at the 13-14 position as indicated by the higher binding affinity for the GRP receptor of BIM-26028 (Leu$^{13}$-Ψ-Leu$^{14}$) as compared to BIM-26025 (His$^{12}$-Ψ-Leu$^{13}$), BIM-26026 (Ala$^9$-Ψ-Val$^{10}$), BIM-26030 (Gly$^{11}$-Ψ-His$^{12}$), and BIM-26034 (Gln$^7$Ψ-Trp$^8$). In Table I, it can also been seen that peptides surprising lack affinity for the NMB receptor. Thus, these peptides, used as therapeutics, will be selective for the GRP receptor and not be prone to adverse side effects resulting from the activation of the NMB receptor.

Table II shows either the inhibition (IC$_{50}$) or stimulation (EC$_{50}$) of [$^3$H] Thymidine uptake by cultured 3T3 cells. In Table II, it can be seen that these peptides are both either potent agonists or antagonist of Thymidine uptake, a precursor to cell proliferation. In general, compounds having the non-peptide bond at the active site of the peptide are antagonists while compounds having the non-peptide bond at any position other than the active site of the peptide are agonists. However, BIM-26027 surprisingly stimulated thymidine uptake, and therefore is an agonist and not an antagonist.

TABLE II

Thymidine Uptake

| PEPTIDE | IC$_{50}$ |
|---|---|
| BIM-26028 | 16.38 |
| BIM-26068 | 26.33 |
| BIM-26099 | 19.70 |
| BIM-26100 | 12.48 |
| BIM-26101 | 34.40 |
| BIM-26113 | 2.43 |
| BIM-26114 | 6.63 |
| BIM-26115 | 10.46 |
| BIM-26116 | 2.45 |
| BIM-26117 | 2.16 |
| BIM-26120 | 23.5 |
| BIM-26136 | 0.477 |
| BIM-26137 | 6.290 |
| BIM-26138 | 8.747 |
| BIM-26139 | 28.40 |
| BIM-26156 | 4.63 |
| BIM-26157 | 0.10 |
| BIM-26158 | 4.99 |
| BIM-26159 | 0.09 |
| BIM-26161 | 1.60 |
| BIM-26163 | 16.02 |
| BIM-26164 | 10.42 |
| BIM-26166 | 0.739 |
| BIM-26167 | 3.38 |
| BIM-26168 | 3.74 |
| BIM-26173 | 2.695 |
| BIM-26174 | 17.81 |
| BIM-26175 | 8.88 |
| BIM-26181 | 5.29 |
| BIM-26186 | 49.82 |
| BIM-26189 | 0.214 |
| BIM-26190 | 1.55 |
| BIM-26211 | 5.157 |
| PEPTIDE | EC$_{50}$ |
| BIM-26027 | 0.07 |
| BIM-26096 | 3.00 |

Table II also shows that when statine replaces the A$^{13}$ and A$^{14}$ residues of a full-length bombesin analog, the resultant analog, BIM-26096, causes an increase in thymidine uptake and is therefore an agonist. However, Table II also shows that when statine or AHPPA replaces the A$^{13}$ and A$^{14}$ residues of a truncated bombesin analog, e.g., BIM-26164, the resultant analog is an antagonist. Additionally, both Table I and Table II show that the deletion of residues A$^1$ through A$^5$ provides for more potent bombesin analogs.

Bombesin analogs are useful in cancer therapy. E.g., see, Alexander et al., 1988, Pancreas 3:297, and Alexander et al., 1988, Cancer Research 48:1439-1441, hereby incorporated by reference. Alexander et al. showed that chronic bombesin treatment inhibited the growth of human ductal adenocarcinoma transplanted into athymic mice. These results were surprising for bombesin stimulates the growth of normal pancreatic tissue. The demonstration of both stimulatory and inhibitory activity of bombesin suggests that bombesin interacts differently in normal and neoplastic tissues.

These observations prompted us to evaluate the effect of BIM-26096 on the in vitro growth of a pancreatic tumor cell line (AR42J, ATCC No. CRL1492). For these experiments, AR42J cells were subcultured into a 24-well culture plate in Dulbecco's modified Eagle's medium containing 10% fetal calf serum and various concentrations (0.1-100 nM) of BIM-26096. After 36 hr. of incubation, the cells were removed with a trypsin/EDTA solution and the number of cells were determined using a Coulter counter. The results are as follows:

| Treatment | Cell Count (% Control) |
|---|---|
| Control | 100 |
| BIM-26096 | |
| (0.1 nM) | 78 |
| (1.0 nM) | 73 |
| (10 nM) | 56 |
| (100 nM) | 52 |

These results indicate that the bombesin agonist, BIM-26096, has in vitro antiproliferative activity against the AR42J rat pancreas tumor.

Bombesin and Bombesin analogs have been shown to inhibit the effect of interleukin-2 (IL-2) (Fink et al., 1988, Klin. Wochenschr. 66, Suppl. 13, 273). Since IL-2 causes T lymphocytes to proliferate, it is possible that Bombesin antagonists may prevent the inhibitory effect of Bombesin or its analogs on IL-2. IL-2 stimulated lymphocytes are capable of effectively lysing small cell lung carcinoma cells in vitro. Although Bombesin antagonists have a direct antiproliferative effect on neoplastic tissues, they may also favor proliferation of lymphocytes having lytic activity for small cell lung carcinoma.

Other Embodiments

Other embodiments are within the following claims.

For example, as is mentioned above, there are a number of other peptide families from which agonists or antagonists can be made according to the invention. Some of these families are substance P and related peptides, vasoactive intestinal peptide (VIP) and related peptides, and neurotensin and related peptides. The number of peptides in each family on which antagonists or agonists can be based is large. For example, there are at least 10 currently-known peptides in the VIP family, including sauvagine and urotensin. In addition, there have been isolated seven natural bradykinin-like peptides. Neurotensin has two peptide bonds which advantageously can be replaced by non-peptide bonds: Ile-Leu and Tyr-Ile. In addition, neurotensin antagonists can be missing any or all of the N-terminal seven amino acid residues, as it has been shown (Granier et al. (1984) Eur. J. Biochem. 124: 117) that they are not needed for biological activity and binding. Screening of neurotensin antagonists can be by binding to SCLC receptors. Gastrin releasing peptides (GRP) and related peptides (e.g., Neuromedin C (GRP 18-27)) have a bond between amino acid residues 13 and 14 which can be replaced with a non-peptide bond to form a GRP antagonist. Other peptides for which antagonists can be made according to the invention are ACTH and related peptides, and angiotensin and related peptides. In addition, LHRH and LHRH agonists can be made into antagonists according to the invention. The same may also apply to lymphokines such as interleukins and to growth factors such as EGF, IGF, and their biologically active fragments. Such embodiments are also contemplated.

What is claimed is:

1. A peptide of the formula:

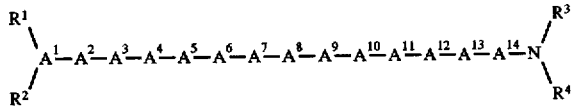

wherein

A$^1$ is D- or L- isomer of pGlu, or deleted;

A$^2$ is Gln, Asn, Gly, Ala, Leu, Ile, Nle, Abu, Met, Val, Phe, p-X-Phe in which X is F, Cl, Br, OH, or CH$_3$, Trp, β-Nal, or deleted;

$A^3$ is the D- or L- isomer selected from Arg and Lys, or deleted;

$A^4$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^5$ is Gly, the D- or L- isomer selected from Gln, Asn, Ala, Leu, Ile, Nle, Abu, Met, Val, Phe, p-X-Phe in which x is F, Cl, Br, OH, or $CH_3$, Trp and β-Nal, or deleted;

$A^6$ is Gly, the D- or L- isomer selected from Gln, Asn, Ala, N—Ac-D-Ala, Leu, Ile, Nle, Abu, Met, Val, Phe, p-X-Phe in which X is F, Cl, Br, OH, or $CH_3$, Trp, and β-Nal, or deleted;

$A^7$ is Gly, or the D- or L- isomer selected from Gln, Asn, Ala, Leu, Ile, Nle, Abu, Met, Val, Phe, p-X-Phe in which X is F, Cl, Br, OH, or $CH_3$, Trp, Lys, His, and β-Nal;

$A^8$ is Trp or Met;

$A^9$ is Sta, AHPPA, Gly, or the D- or L- isomer selected from Gln, Asn, Ala, Leu, Ile, Nle, Abu, Met, Val, Phe, p-X-Phe in which X is F, Cl, Br, OH, or $CH_3$, Trp, and β-Nal;

$A^{10}$ is Sta, AHPPA, Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Sta, AHPPA, Gly, or the D- or L- isomer selected from Ala, and Phe;

$A^{12}$ is Sta, AHPPA, or the D- or L- isomer selected from His, Phe, and p-X-Phe in which X is F, Cl, Br, OH, or $CH_3$;

$A^{13}$ is Sta, AHPPA, Gly, or the D- or L- isomer selected from Gln, Asn, Ala, Leu, Ile, Nle, Abu, Met, Val, Phe, p-X-Phe in which X is F, Cl, Br, OH, or $CH_3$, Trp, and β-Nal;

$A^{14}$ is Gln, Asn, Gly, Ala, Leu, Ile, Nle, Abu, Met, Val, Phe, p-X-Phe in which X is F, Cl, Br, OH, or $CH_3$, Trp, or β-Nal;

each of $R^1$ and $R^2$, independently, is H, Phenylalkyl, $CO.E_1$ in which $E_1$ is $C_{1-20}$ alkyl, $C_{2-20}$ alkynyl, Phenyl, naphthyl or $C_{7-10}$ Phenylalkyl, or $CO.OE_2$ in which $E_2$ is $C_{1-10}$ alkyl or $C_{7-10}$ Phenylalkyl; and each of $R^3$ and $R^4$, independently, is H, $C_{1-12}$ alkyl, $C_{7-10}$ Phenylalkyl;

provided that when one of $R^1$ and $R^2$ is $CO.E_1$ or $CO.OE_2$, the other must be H; further provided that when $A^1$ is Pglu, one of $R^1$ and $R^2$ must be H and the other must be the portion of Pglu that forms the imine ring, and when the N-terminal amino acid is Saa, one of $R^1$ and $R^2$ must be the $N^\alpha$-substitutent of said Saa; provided that either the carbon atom participating in the amide bond between one and only one pair of neighboring amino acids selected from $A^7$ and $A^8$, $A^8$ and $A^9$, $A^9$ and $A^{10}$, $A^{11}$ and $A^{12}$, $A^{12}$ and $A^{13}$, and $A^{13}$ and $A^{14}$ is a methylene carbon, or one and only one of $A^9$, $A^{10}$, $A^{11}$, $A^{12}$, and $A^{13}$ is Sta or AHPPA; and further provided that the next higher numbered amino acid residue adjacent to Sta or AHPPA must be deleted; or a pharmaceutically acceptable salt thereof.

2. The peptide of claim 1, wherein:

$A^1$ is pGlu, or deleted;

$A^2$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^3$ is the D- or L- isomer selected from Arg and Lys, or deleted;

$A^4$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^5$ is Gln, Asn, Gly, Ala, Leu, Ile, Nle, Abu, Met, Val, Phe, D-Phe, p-X-Phe in which X is F, Cl, Br, OH, or $CH_3$, Trp, β-Nal, D-Ala, or deleted;

$A^6$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^7$ is Gln, Asn, Gly, Ala, Leu, Ile, Nle, Abu, Met, Val, Phe, D-Phe, p-X-Phe in which X is F, Cl, Br, OH, or $CH_3$, Trp, or β-Nal;

$A^8$ is Trp;

$A^9$ is Gln, Asn, Gly, Ala, Leu, Ile, Nle, Abu, Met, Val, Phe, p-X-Phe in which X is F, Cl, Br, OH, or $CH_3$, Trp, or β-Nal;

$A^{10}$ is Gln, Asn, Gly, Ala, Leu, Ile, Nle, Abu, Met, Val, Phe, p-X-Phe in which X is F, Cl, Br, OH, or $CH_3$, Trp, or β-Nal;

$A^{11}$ Gly or D-Ala;

$A^{12}$ is His, Phe, or p-X-Phe in which X is F, Cl, Br, OH, or CH3;

$A^{13}$ is Gln, Asn, Gly, Ala, Leu, Ile, Nle, Abu, Met, Val, Phe, p-X-Phe in which X is F, Cl, Br, OH, or $CH_3$, Trp, or β-Nal; and $A^{14}$ is Gln, Asn, Gly, Ala, Leu, Ile, Nle, Abu, Met, Val, Phe, p-X-Phe in which X is F, Cl, Br, OH, or $CH_3$, Trp, or β-Nal; or a pharmaceutically acceptable salt thereof.

3. The peptide of claim 1, wherein one of $R^1$ and $R^2$ is Phenylpropionyl and the other is H; or a pharmaceutically acceptable salt thereof.

4. The peptide of claim 1, wherein $A^1$ through $A^5$ are deleted and the carbon atom participating in the amide bond between $A^{13}$ and $A^{14}$ is a methylene carbon; or a pharmaceutically acceptable salt thereof.

5. The peptide of claim 1, wherein each of $A^{13}$ and $A^{14}$ independently is Phe or Leu; or a pharmaceutically acceptable salt thereof.

6. The peptide of claim 1, wherein the carbon atom participating in the amide bond between $A^{11}$ and $A^{12}$, $A^{12}$ and $A^{13}$, or $A^{13}$ and $A^{14}$ is a methylene carbon; or a pharmaceutically acceptable salt thereof.

7. The peptide of claim 1, wherein $A^9$ is Gly, or the D- or L- isomer selected from Gln, Asn, Gly, Ala, Leu, Ile, Nle, Abu, Met, Val, Phe, p-X-Phe in which X is F, Cl, Br, OH, or $CH_3$, Trp, and β-Nal;

$A^{10}$ is Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Gly, or the D- or L- isomer selected from Ala, Eaa, and Phe;

$A^{12}$ is D- or L- isomer selected from His, Phe, and p-X-Phe in which X is F, Cl, Br, OH, or $CH_3$; and $A^{13}$ is Gly, or the D- or L- isomer selected from Gln, Asn, Gly, Ala, Leu, Ile, Nle, Abu, Met, Val, Phe, p-X-Phe in which X is F, Cl, Br, OH, or $CH_3$, Trp, Tic, Tip, Oic, Tcc, and β-Nal; or a pharmaceutically acceptable salt thereof.

8. The peptide of claim 1, wherein one and only one of $A^9$, $A^{10}$, $A^{11}$, $A^{12}$ and $A^{13}$ is Sta or AHPPA; or a pharmaceutically acceptable salt thereof.

9. The peptide of claim 1, said peptide having the formula: pGlu-Gln-Arg-Leu-Gly-Asn-Gln-Trp-Ala-Val-Ψ-Gly-His-Leu-Leu-$NH_2$;

or a pharmaceutically acceptable salt thereof.

10. The peptide of claim 1, said peptide having the formula:
pGlu-Gln-Arg-Leu-Gly-Asn-Gln-Trp-Ala-Val-Gly-His-Sta-$NH_2$;
or a pharmaceutically acceptable salt thereof.

11. A peptide of the formula:

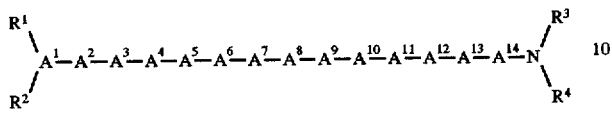

wherein
$A^1$ is D- or L- isomer of pGlu, or deleted;

$A^2$ is Gln, Asn, Gly, Ala, Leu, Ile, Nle, Abu, Met, Val, Phe, p-X-Phe in which X is F, Cl, Br, OH, or $CH_3$, Trp, βNal, or deleted;

$A^3$ is the D- or L- isomer selected from Arg and Lys, or deleted;

$A^4$ is Gln, Asn, Gly, Ala, Leu, Ile, Nle, Abu, Met, Val, Phe, p-X-Phe in which X is F, Cl, Br, OH, or $CH_3$, Trp, βNal, or deleted;

$A^5$ is Gly, the D- or L- isomer selected from Gln, Asn, Ala, Leu, Ile, Nle, Abu, Met, Val, Phe, D-Phe, p-X-Phe in which X is F, Cl, Br, OH, or $CH_3$, Trp and β-Nal, or deleted;

$A^6$ is Gly, the D- or L- isomer selected from Gln, Asn, Ala, N—Ac-D-Ala, Leu, Ile, Nle, Abu, Met, Val, Phe, p-X-Phe in which X is F, Cl., Br, OH, or $CH_3$, pentafluoro-Phe, Trp, and β-Nal, or deleted;

$A^7$ is Saa;

$A^8$ is Trp or Met;

$A^9$ is Sta, AHPPA, Gly, or the D- or L- isomer selected from Gln, Asn, Ala, Leu, Ile, Nle, Abu, Met, Val, Phe, p-X-Phe in which X is F, Cl, Br, OH, or $CH_3$, Trp, and βNal;

$A^{10}$ is Sta, AHPPA, Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Sta, AHPPA, Gly, or the D- or L- isomer selected from Ala, Eaa, and Phe;

$A^{12}$ is Sta, AHPPA, or the D- or L- isomer selected from His, Phe, and p-X-Phe in which X is F, Cl, Br, OH, or $CH_3$;

$A^{13}$ is Sta, AHPPPA, Gly or the D- or L- isomer selected from Gln, Asn, Ala, Leu, Ile, Nle, Abu, Met, Val, Phe, p-X-Phe in which X is F, Cl, Br, OH, or $CH_3$, Trp, Pro, Tic, Tip, Oic, Tcc, and β-Nal;

$A^{14}$ is Gln, Asn, Gly, Ala, Leu, Ile, Nle, Abu, Met, Val, Phe, p-X-Phe in which X is F, Cl, Br, OH, or $CH_3$, Trp, Tic, Tip, Oic, Tcc, or β-Nal;

each of $R^1$ and $R^2$, independently, is H, $C_{1-12}$ alkyl, $C_{7-10}$ Phenylalkyl, $CO.E_1$ in which $E_1$ is $C_{1-20}$ alkyl, $C_{2-20}$ alkenyl, $C_{2-20}$ alkynyl, Phenyl, naphthyl, or $C_{7-10}$ Phenylalkyl, or $CO.OE_2$ in which $E_2$ is $C_{1-10}$ alkyl or $C_{7-10}$ Phenylalkyl; and each of $R^3$ and $R^4$, independently, is H, $C_{1-12}$ alkyl, or $C_{7-10}$ Phenylalkyl;

provided that when one of $R^1$ and $R^2$ is $CO.E_1$ or $CO.OE_2$, the other must be H; further provided that when $A^1$ is pGlu, one of $R^1$ and $R^2$ must be H and the other must be the portion of pGlu that forms the imine ring, and when the N-terminal amino acid is Saa, one of $R^1$ and $R^2$ must be the Nα-substitutent of said Saa; provided that either the carbon atom participating in the amide bond between one and only one pair of neighboring amino acids selected from $A^7$ and $A^8$, $A^8$ and $A^9$, $A^9$ and $A^{10}$, $A^{11}$ and $A^{12}$, $A^{12}$ and $A^{13}$, and $A^{13}$ and $A^{14}$ is a methylene carbon, or one and only one of $A^9$, $A^{10}$, $A^{11}$, $A^{12}$, and $A^{13}$ is Sta or AHPPA; and further provided that the next higher numbered amino acid residue adjacent to Sta or AHPPA must be deleted; or a pharmaceutically acceptable salt thereof.

12. The peptide of claim 11, wherein
$A^9$ is Gly, or the D- or L- isomer selected from Gln, Asn, Gly, Ala, Leu, Ile, Nle, Abu, Met, Val, Phe, p-X-Phe in which X is F, Cl, Br, OH, or $CH_3$, Trp, and β-Nal;

$A^{10}$ is Gln, Asn, Gly, Ala, Leu, Ile, Nle, Abu, Met, Val, Phe, p-X-Phe in which X is F, Cl, Br, OH, or $CH_3$, Trp, Thr, or β-Nal;

$A^{11}$ is Gly, or the D- or L- isomer selected from Ala, Eaa, and Phe;

$A^{12}$ is the D- or L- isomer selected from His, Phe, and p-X-Phe in which X is F, Cl, Br, OH, or $CH_3$; and $A^{13}$ is Gly, or the D- or L- isomer selected from Gln, Asn, Gly, Ala, Leu, Ile, Nle, Abu, Met, Val, Phe, p-X-Phe in which X is F, Cl, Br, OH, or $CH_3$, Trp, Pro, Tic, Tip, Oic, Tcc, and β-Nal; or a pharmaceutically acceptable salt thereof.

13. The peptide of claim 12, wherein $A^7$ is Sar, or the D- or L- isomer selected from Pro, homo-Pro, N-me-Ala, Tic, Tip, Tcc, and Oic; or a pharmaceutically acceptable salt thereof.

14. The peptide of claim 12, wherein $A^{11}$ is Eaa.

15. The peptide of claim 11, wherein one and only one of $A^9$, $A^{10}$, $A^{11}$, $A^{12}$ and $A^{13}$ is Sta or AHPPA; or a pharmaceutically acceptable salt thereof.

16. A peptide of the formula:

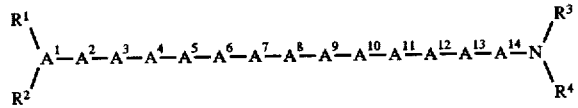

wherein
$A^1$ is the D- or L- isomer of pGlu, or deleted;

$A^2$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^3$ is the D- or L- isomer selected from Arg and Lys, or deleted;

$A^4$ is Gln, Asn, Gly, Ala, Leu, Ile, Nle, Abu, Met, Val, Phe, p-X-Phe in which X is F, Cl, Br, OH, or $CH_3$, Trp, β-Nal, or deleted;

$A^5$ is Gly, the D- or L- isomer selected from Gln, Asn, Ala, Leu, Ile, Nle, Abu, Met, Val, Phe, D-Phe, p-X-Phe in which X is F, Cl, Br, OH, or $CH_3$, Trp and β-Nal, or deleted;

$A^6$ is Gly, the D- or L- isomer selected from Gln, Asn, Ala, N—Ac-D-Ala, Leu, Ile, Nle, Abu, Met, Val, Phe, p-X-Phe in which X is F, Cl, Br, OH, or $CH_3$, pentafluoro-Phe, Trp, and β-Nal, or deleted;

$A^7$ is Gly, or the D- or L- isomer selected from Gln, Asn, Ala, Leu, Ile, Nle, Abu, Met, Val, Phe, D-Phe, p-X-Phe in which X is F, Cl, Br, OH, or $CH_3$, Trp, Lys, His, Saa, and β-Nal;

$A^8$ is Trp or Met;

$A^9$ is Sta, AHPPA, Gly, or the D- or L- isomer selected from Gln, Asn, Ala, Leu, Ile, Nle, Abu, Met, Val, Phe, p-X-Phe in which X is F, Cl, Br, OH, or $CH_3$, Trp, and β-Nal;

$A^{10}$ is Gln, Asn, Gly, Ala, Leu, Ile, Nle, Abu, Met, Val, Phe, p-X-Phe in which X is F, Cl, Br, OH, or $CH_3$, Trp, Thr, or β-Nal;

A¹¹ is or Eaa;

A¹² is Sta, AHPPA, the D- or L- isomer selected from His, Phe, and p-X-Phe in which X is F, Cl, Br, OH, or CH₃;

A¹³ is Sta, AHPPA, Gly, or the D- or L- isomer selected from Gln, Asn, Ala, Leu, Ile, Nle, Abu, Met, Val, Phe, p-X-Phe in which X is F, Cl, Br, OH, or CH₃, Trp, Pro, Tic, Tip, Oic, Tcc, and β-Nal;

A¹⁴ is Gln, Asn, Gly, Ala, Leu, Ile, Nle, Abu, Met, Val, Phe, p-X-Phe in which X is F, Cl, Br, OH, or CH₃, Trp, Tic, Tip, Oic, Tcc, or β-Nal;

each of $R^1$ and $R^2$, independently, is H, $C_{1-12}$ alkyl, $C_{7-10}$ Phenylalkyl, $CO.E_1$ in which $E_1$ is $C_{1-20}$ alkyl, $C_{2-20}$ alkenyl, $C_{2-20}$ alkynyl, Phenyl, naphthyl, or $C_{7-10}$ Phenylalkyl, or $CO.OE_2$ in which $E_2$ is $C_{1-10}$ alkyl or $C_{7-10}$ Phenylalkyl; and each of $R^3$ and $R^4$, independently, is H, $C_{1-12}$ alkyl, or $C_{7-10}$ Phenylalkyl;

provided that when one of $R^1$ and $R^2$ is $CO.E_1$ or $CO.OE_2$, the other must be H; further provided that when A¹ is pGlu, one of $R^1$ and $R^2$ must be H and the other must be the portion of pGlu that forms the imine ring, and when the N-terminal amino acid is Saa, one of $R^1$ and $R^2$ must be the $N^\alpha$-substitutent of said Saa; provided that either the carbon atom participating in the amide bond between one and only one pair of neighboring amino acids selected from A⁷ and A⁸, A⁸ and A⁹, A⁹ and A¹⁰, A¹¹ and A¹², A¹² and A¹³, and A¹³ and A¹⁴ is a methylene carbon, or one and only one of A⁹, A¹⁰, A¹¹, A¹², and A¹³ is Sta or AHPPA; and further provided that the next higher numbered amino acid residue adjacent to Sta or AHPPA must be deleted; or a pharmaceutically acceptable salt thereof.

17. The peptide of claim 16, wherein

A⁹ is Gly, or the D- or L- isomer selected from Gln, Asn, Gly, Ala, Leu, Ile, Nle, Abu, Met, Val, Phe, p-X-Phe in which X is F, Cl, Br, OH, or CH₃, Trp, and β-Nal;

A¹⁰ is Gln, Asn, Gly, Ala, Leu, Ile, Nle, Abu, Met, Val, Phe, p-X-Phe in which X is F, Cl, Br, OH, or CH₃, Trp, Thr, or β-Nal;

A¹¹ is Eaa;

A¹² is the D- or L- isomer selected from His, Phe, and p-X-Phe in which X is F, Cl, Br, OH, or CH₃; and A¹³ is Gly, or the D- or L- isomer selected from Gln, Asn, Gly, Ala, Leu, Ile, Nle, Abu, Met, Val, Phe, p-X-Phe in which X is F, Cl, Br, OH, or CH₃, Trp, Pro, Tic, Tip, Oic, Tcc, and β-Nal; or a pharmaceutically acceptable salt thereof.

18. The peptide of claim 17, wherein A¹¹ β-Ala, γ-aminobytyric acid, or 5-aminopentanoic acid; or a pharmaceutically acceptable salt thereof.

19. The peptide of claim 16, wherein one and only one of A⁹, A¹², and A¹³ is Sta or AHPPA; or a pharmaceutically acceptable salt thereof.

20. A peptide of the formula:

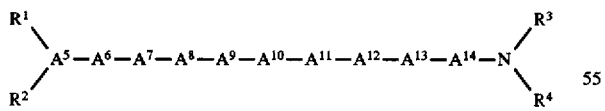

wherein

A⁵ is Gln, Asn, Gly, Ala, Leu, Ile, Nle, Abu, Met, Val, Phe, D-Phe, p-X-Phe in which X is F, Cl, Br, OH, or CH₃, Trp, β-Nal, or deleted;

A⁶ is Gln, Asn, Gly, Ala, D-Ala, N-Ac-D-Ala, Leu, Ile, Nle, Abu, Met, Val, Phe, p-X-Phe in which X is F, Cl, Br, OH, or CH₃, Trp, p-Glu, Trp, β-Nal, or deleted;

A⁷ is Gln, Asn, Gly, Ala, Leu, Ile, Nle, Abu, Met, Val, Phe, D-Phe, p-X-Phe in which X is F, Cl, Br, OH, or CH₃, Trp, Lys, His, or β-Nal;

A⁸ is Trp or Met;

A⁹ is the D- or L-isomer selected from Gln, Asn, Gly, Ala, Leu, Ile, Nle, Abu, Met, Val, Phe, p-X-Phe in which X is F, Cl, Br, OH, or CH₃, Trp, and β-Nal;

A¹⁰ is Gln, Asn, Gly, Ala, Leu, Ile, Nle, Abu, Met, Val, Phe, p-X-Phe in which X is F, Cl, Br, OH, or CH₃, Trp, Thr, or β-Nal;

A¹¹ is Gly, or the D- or L- isomer selected from Ala and Phe;

A¹² is the D- or L- isomer selected from His, Phe, and p-X-Phe in which X is F, Cl, Br, OH, or CH₃;

A¹³ is Gln, Asn, Gly, Ala, Leu, Ile, Nle, Abu, Met, Val, Phe, p-X-Phe in which X is F, Cl, Br, OH, or CH₃, Trp, or β-Nal;

A¹⁴ is Gln, Asn, Gly, Ala, Leu, Ile, Nle, Abu, Met, Val, Phe, p-X-Phe in which X is F, Cl, Br, OH, or CH₃, Trp, or β-Nal;

each of $R^1$ and $R^2$, independently, is H, $C_{1-12}$ alkyl, $C_{7-10}$ Phenylalkyl, $CO.E_1$ in which $E_1$ is $C_{1-20}$ alkyl, $C_{2-20}$ alkenyl, $C_{2-20}$ alkynyl, Phenyl, naphthyl, or $C_{7-10}$ Phenylalkyl, or $CO.OE_2$ in which $E_2$ is $C_{1-10}$ alkyl or $C_{7-10}$ Phenylalkyl; and each of $R^3$ and $R^4$, independently, is H, $C_{1-12}$ alkyl, or $C_{7-10}$ Phenylalkyl;

provided that when one of $R^1$ and $R^2$ is $CO.E_1$ or $CO.OE_2$, the other must be H; further provided that when A¹ is pGlu, one of $R^1$ and $R^2$ must be H and the other must be the portion of pGlu that forms the imine ring, and when the N-terminal amino acid is Saa, one of $R^1$ and $R^2$ must be the $N^\alpha$-substitutent of said Saa; and further provided that the carbon atom participating in the amide bond between A¹³ and A¹⁴ is either a carbonyl carbon or a methylene carbon; or a pharmaceutically acceptable salt thereof.

21. The peptide of claim 20, wherein

A⁵ is deleted;

A⁶ is Gln, Asn, Gly, Ala, D-Ala, N—Ac-D-Ala, Leu, Ile, Nle, Abu, Met, Val, Phe, p-X-Phe in which X is F, Cl, Br, OH, or CH₃, Trp, p-Glu, Trp, β-Nal, or deleted;

A⁷ is Gln, Asn, Gly, Ala, Leu, Ile, Nle, Abu, Met, Val, Phe, D-Phe, p-X-Phe in which X is F, Cl, Br, OH, or CH₃, Trp, Lys, His, or β-Nal;

A⁸ is Trp or Met;

A⁹ is the D- or L-isomer selected from Gln, Asn, Gly, Ala, Leu, Ile, Nle, Abu, Met, Val, Phe, p-X-Phe in which X is F, Cl, Br, OH, or CH₃, Trp, and β-Nal;

A¹⁰ is Gln, Asn, Gly, Ala, Leu, Ile, Nle, Abu, Met, Val, Phe, p-X-Phe in which X is F, Cl, Br, OH, or CH₃, Trp, Thr, or β-Nal;

A¹¹ is Gly, or the D- or L- isomer selected from Ala and Phe;

A¹² is the D- or L- isomer selected from His, Phe, and p-X-Phe in which X is F, Cl, Br, OH, or CH₃;

A¹³ is Gln, Asn, Gly, Ala, Leu, Ile, Nle, Abu, Met, Val, Phe, p-X-Phe in which X is F, Cl, Br, OH, or CH₃, Trp, or β-Nal; and A¹⁴ is Gln, Asn, Gly, Ala, Leu, Ile, Nle, Abu, Met, Val, Phe, p-X-Phe in which X is F, Cl, Br, OH, or CH₃, Trp, or β-Nal; or a pharmaceutical salt thereof.

* * * * *